(12) United States Patent
Nakamura et al.

(10) Patent No.: US 11,051,792 B2
(45) Date of Patent: Jul. 6, 2021

(54) SPERM SAMPLER DRIVING DEVICE

(71) Applicant: TENGA Co., Ltd., Tokyo (JP)

(72) Inventors: Kengo Nakamura, Tokyo (JP); Kai Endo, Tokyo (JP)

(73) Assignee: TENGA CO., LTD, Tokyo (JP)

( * ) Notice: Subject to any disclaimer, the term of this patent is extended or adjusted under 35 U.S.C. 154(b) by 292 days.

(21) Appl. No.: 16/408,304

(22) Filed: May 9, 2019

(65) Prior Publication Data

US 2020/0178943 A1 Jun. 11, 2020

(30) Foreign Application Priority Data

Dec. 6, 2018 (JP) .............................. JP2018-229008

(51) Int. Cl.
| | |
|---|---|
| *A61B 10/00* | (2006.01) |
| *A61F 5/453* | (2006.01) |
| *A61F 5/451* | (2006.01) |
| *A61H 19/00* | (2006.01) |
| *A61F 5/41* | (2006.01) |

(52) U.S. Cl.
CPC .......... *A61B 10/0058* (2013.01); *A61F 5/451* (2013.01); *A61F 5/453* (2013.01); *A61H 19/32* (2013.01); *A61F 5/41* (2013.01)

(58) Field of Classification Search
CPC ................ A61B 10/0058; A61H 19/32; A61H 2201/1253; A61H 2201/1261; A61H 2201/1671; A61H 2201/1215; A61H 2201/5079; A61H 2201/1207; A61H 2205/087; A61H 19/30; A61H 2201/5069; A61H 19/00; A61H 23/0254; A61F 5/41; A61F 5/453; A61F 6/04; A61F 2005/411–418; A61F 5/451

See application file for complete search history.

(56) References Cited

FOREIGN PATENT DOCUMENTS

| | | | |
|---|---|---|---|
| CN | 107049447 A | * | 8/2017 |
| EP | 2777679 A1 | | 9/2014 |
| JP | 2014-533163 A | | 12/2014 |
| JP | 2016-209502 A | | 12/2016 |
| WO | WO-2016132462 A1 | * | 8/2016 ........... A61H 9/0057 |

* cited by examiner

*Primary Examiner* — Kaylee R Wilson
(74) *Attorney, Agent, or Firm* — Masuvalley & Partners (57) ABSTRACT

To include a rotating holder 30 that is rotatably arranged in an opening of a casing 10 and detachably holds a part of a sperm sampler, a motor 50 that rotates and drives the rotating holder, a control unit 60, a battery 70, a single switch 20, 67, and an angular speed sensor 61 that detects an angular speed of the casing 10, where the control unit changes a rotation direction and a rotation speed of the motor according to a change in a turning angle of the casing 10.

2 Claims, 11 Drawing Sheets

A-A CROSS-SECTIONAL VIEW

A-A CROSS-SECTIONAL VIEW

B-B CROSS-SECTIONAL VIEW

SPERM SAMPLER DRIVING DEVICE

RELATED APPLICATIONS

This application claims priority under 35 U.S.C. § 119 from Japanese Patent Application No. 2018-229008, filed Dec. 6, 2018, entitled "Sperm Sampler Driving Device", which is incorporated herein by reference in its entirety.

TECHNICAL FIELD

The present invention relates to a sperm sampler driving device that can improve the efficiency of sperm sampling by a sperm sampler, which has been conventionally used according to demands for medical studies and treatment, as well as social demands such as prevention of sex crimes, prevention of prostitutions, and spread of sexually transmitted diseases.

BACKGROUND ART

According to the requirements for medical studies and treatment, various types of sperm samplers (ejaculation facilitating devices) for sampling sperm of a male have been proposed. For example, a sperm sampler is used for medical needs such as examining the sexual function of a husband based on sampled sperm in order to determine the cause of infertility between the husband and his wife, treating sexual dysfunctions, and obtaining and storing sperm for artificial insemination. Further, in order to satisfy various social needs such as prevention of sex crimes, prevention of prostitutions, reduction of the number of people infected with sexually transmitted diseases as satisfying personal sexual desire, there are conventionally known simple sperm samplers that are inexpensively available and are of disposable type or washable type so that they cause no sanitary or health issues.

For example, Japanese Patent Application Laid-open No. 2016-209502 discloses a rotary driving device for a sperm receiver including an attachment part for inserting a cylindrical sperm receiver to which a penis can be inserted, an attachment part for the sperm receiver that has an air bag to be applied in a gap between the attachment part and the sperm receiver to fill the gap, and a driving device that rotates and drives the attachment part.

Japanese Patent Application Laid-open No. 2014-533163 discloses a device for sexual stimulation for a male including a sleeve having elasticity including a hollow part in which a penis is inserted, and a vibration motor that rotates the sleeve, where the device being configured to increase or decrease the rotation speed of the vibration motor by a signal generated by a force sensor that is actuated upon reception of a force from the penis.

Both of the devices according to Japanese Patent Application Laid-open No. 2016-209502 and Japanese Patent Application Laid-open No. 2014-533163 electrically rotate and turns a sperm receiver or the like to which a penis is inserted to slide and rub the penis, thereby facilitating ejaculation by stimulating the penis in a rotation direction.

However, both of the ejaculation facilitating devices have problems such as requiring many switches for changing the rotation speed, the rotation mode, and the like of the sperm receiver during use with a penis being inserted in the sperm receiver, requiring complicated switching operations, and enlargement of actual devices.

SUMMARY OF THE INVENTION

The present invention has been achieved in view of the above problems, and an object of the present invention is to provide a sperm sampler driving device that allows to arbitrarily and finely adjust a rotation speed and a rotation direction of a sperm sampler by only operating to adjust a turning direction posture (an angle) of the device without performing any complicated operations with a plurality of switches, in a device configuration such that stimulation to a penis is facilitated by electrically rotating a core member relative to the penis in a state where the penis is inserted into the core member.

In order to achieve the above object, a sperm sampler driving device according to the present invention is a unit that detachably holds a sperm sampler and rotates a held sperm sampler, the sperm sampler driving device including a casing that has one end being open and is manually holdable, a rotating holder that is rotatably arranged in an opening of the casing and detachably holds a part of the sperm sampler, a motor that is arranged in the casing and rotates and drives the rotating holder, a control unit, a battery as power supply for the motor and the control unit, a single switch that is arranged on an outer face of the casing and turns on and off power supply from the battery to the motor, and an angular speed sensor that detects a turning angular speed of the casing, wherein the control unit changes a rotation direction and a rotation speed of the motor according to a change in a turning angle of the casing.

According to the present invention, a rotation speed and a rotation direction of a sperm sampler can be arbitrarily and finely adjusted by operating and adjusting a turning direction posture (an angle) of a device with a single switch without performing any complicated switch operations with a plurality of switches.

DESCRIPTION OF EMBODIMENTS

The present invention will be described below in detail with an embodiment illustrated in the drawings.

<Basic Configuration of Sperm Sampler Driving Device>

Figure 1A:
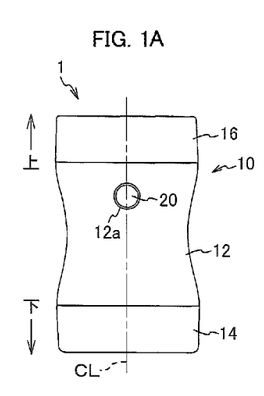
FIG. 1A to FIG. 1F are respectively a front view, a left side view, a right side view, a top view, a bottom view, and a rear view illustrating an exterior configuration of a sperm sampler driving device according to one embodiment of the present invention.
Figure 1B:
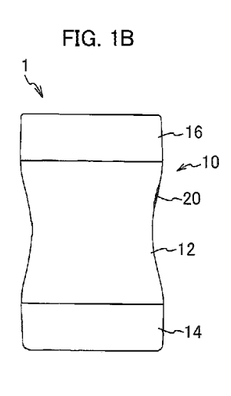
Figure 1C:
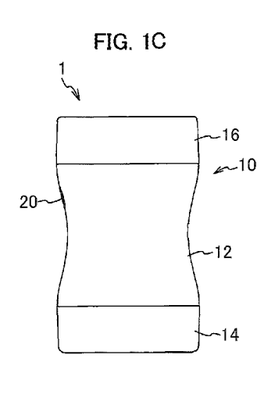
Figure 1D:
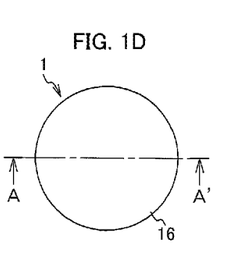
Figure 1E:
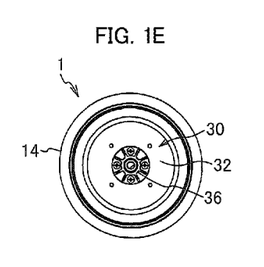
Figure 1F:
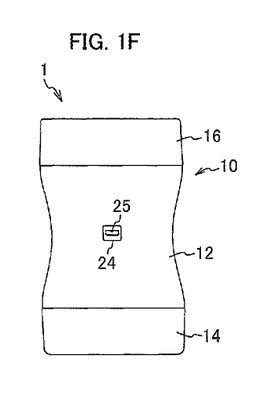
Figure 2A:
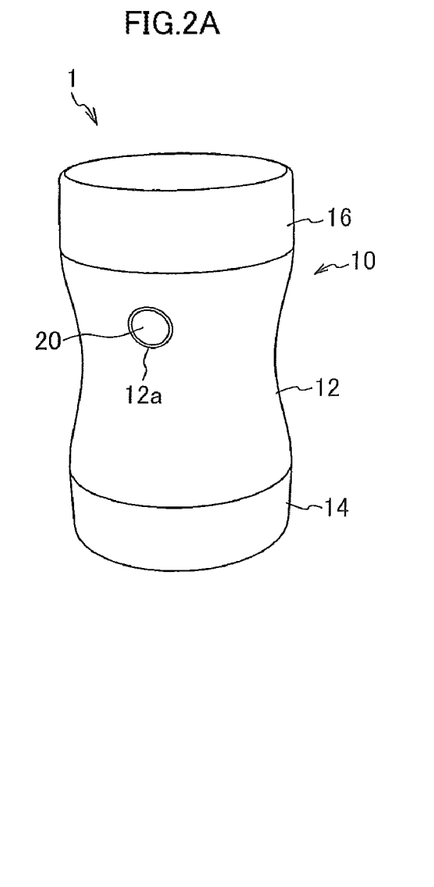
FIG. 2A and FIG. 2B are respectively a perspective view and an A-A cross-sectional view of FIG. 1D of the driving device.
Figure 2B:
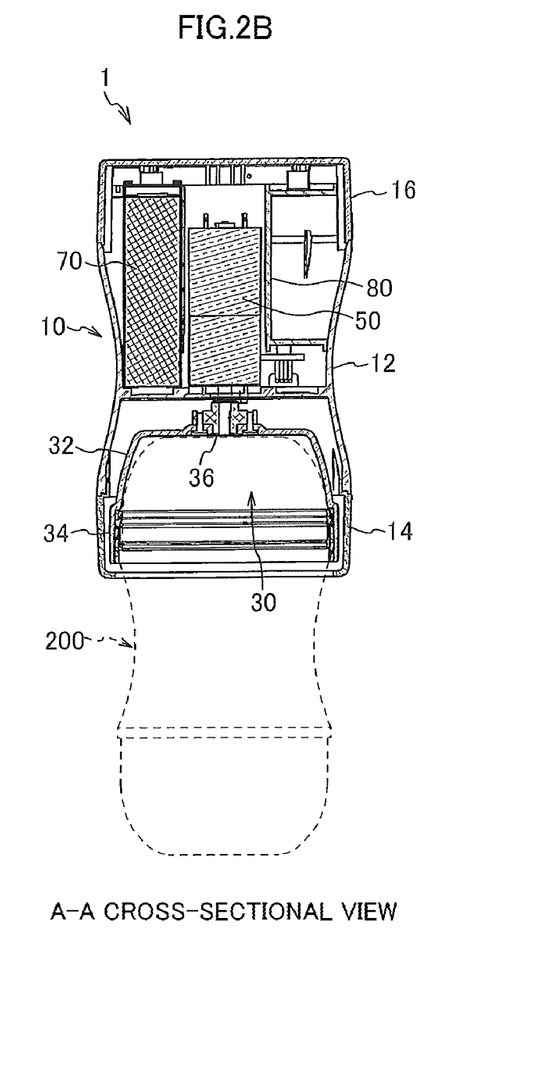
Figure 3:
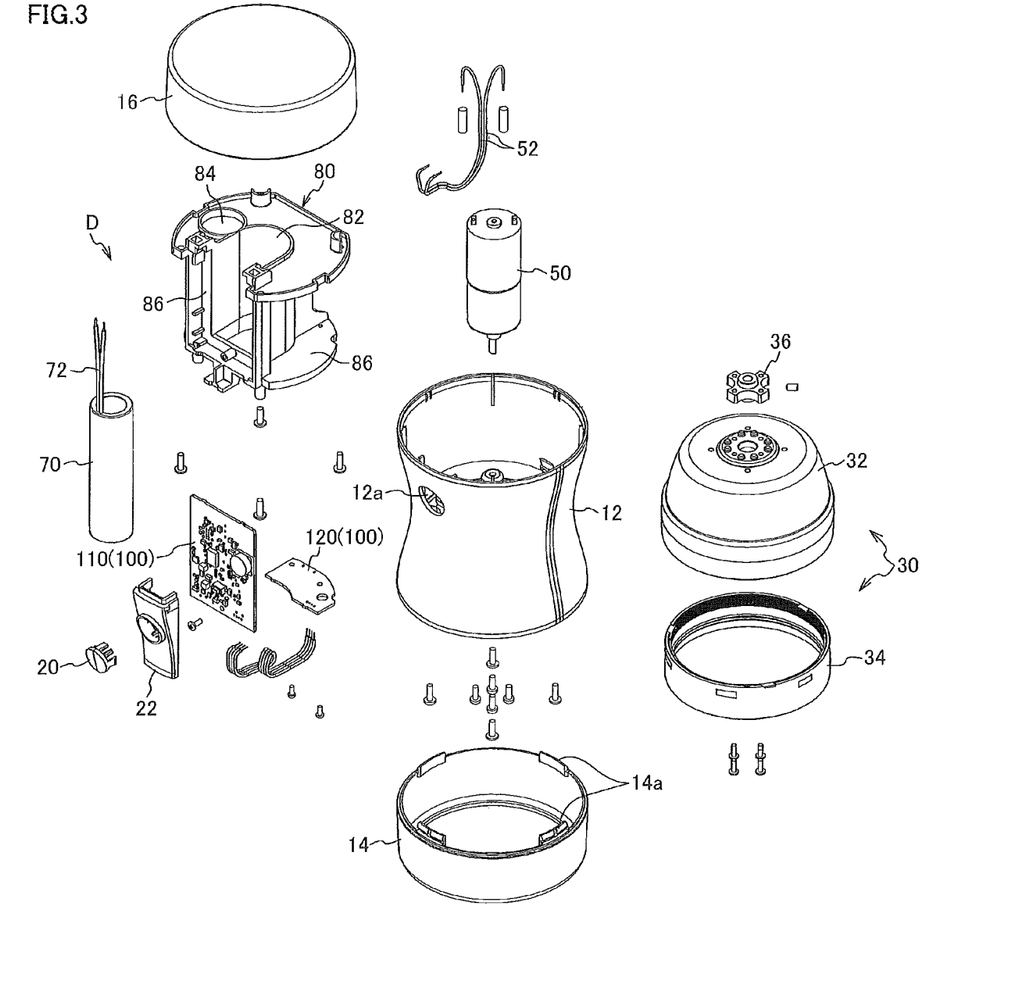
FIG. 3 is an exploded perspective view of respective parts constituting the driving device.
Figure 4:
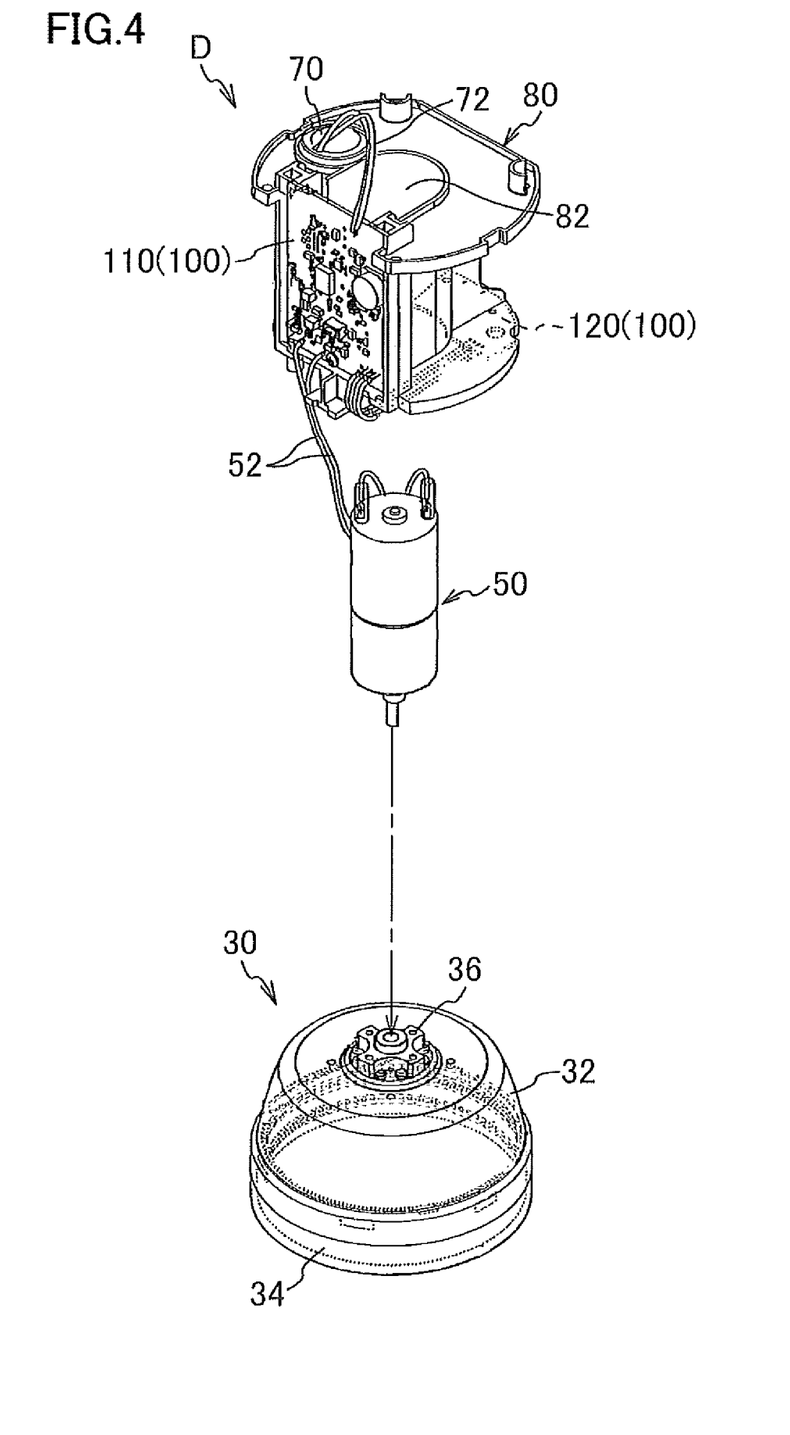
FIG. 4 is a perspective view illustrating respective assembled states of a driving mechanism and a rotor.
Figure 5A:
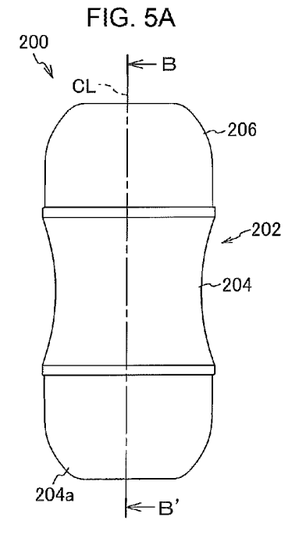
FIG. 5A to FIG. 5E are respectively a front view, a top view, a bottom view, a perspective view, and a B-B cross sectional view illustrating a configuration of one example of a sperm sampler applicable to the driving device.
Figure 5B:
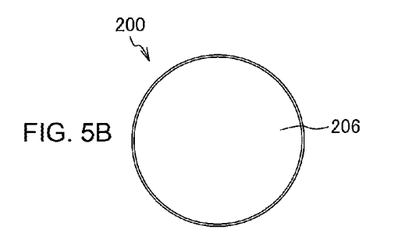
Figure 5C:
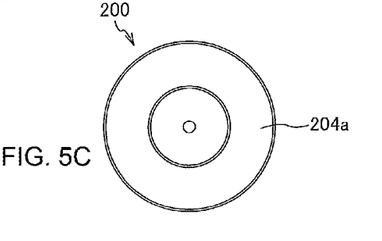
Figure 5D:
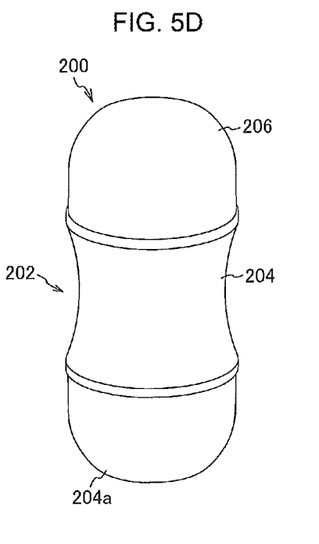
Figure 5E:
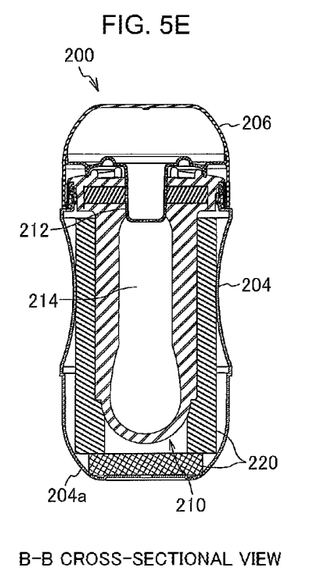

FIG. 1A to FIG. 1F are respectively a front view, a left side view, a right side view, a top view, a bottom view, and a rear view illustrating an exterior configuration of a sperm sampler driving device according to one embodiment of the present invention, FIG. 2A and FIG. 2B are respectively a perspective view and an A-A cross-sectional view of the driving device, FIG. 3 is an exploded perspective view of respective parts constituting the driving device, and FIG. 4 is a perspective view illustrating respective assembled states of a driving mechanism and a rotor.

A sperm sampler driving device 1 according to the present invention is a unit that detachably holds a sperm sampler 200 and rotates and turns the held sperm sampler about a center axis CL thereof.

The sperm sampler driving device 1 (hereinafter, "the driving device 1") generally includes a casing 10 that is manually holdable and has one end being open, a rotating holder (rotor) 30 that is rotatably arranged in an opening of the casing and detachably holds a part of the sperm sampler, a motor 50 that is arranged in the casing and rotates and drives the rotating holder, a control unit (control circuit) 60 (see FIG. 10), a battery 70 as power supply for the motor and the control circuit and the like, a switch 20 that is arranged on an outer face of the casing and turns on and off power supply from the battery to the motor, and an angular speed sensor (gyro sensor) 61 (see FIG. 10) that detects an angular speed of the casing.

In a state where power is supplied from the battery 70 by turning ON the switch 20 (67), the control unit 60 changes a rotation direction and a rotation speed of the motor according to a change in rotation direction angular speed about the center axis CL of the casing 10 that is detected by the angular speed sensor 61.

The casing 10 includes a substantially cylindrical intermediate case part 12 having both ends being open in an axial direction, a cylindrical lower case part 14 that is attached to a lower opening of the intermediate casing part in an aligned state and is penetrated in an upward and downward direction, and an upper case part (cover) 16 that is attached in an aligned state to an upper opening of the intermediate case part and is only open at a lower end. The case parts 12, 14, 16 are constituted of relatively rigid plastic. To the lower opening and the upper opening of the intermediate case part 12, a peripheral edge of the lower case part 14 and a peripheral edge of the upper case part 16 are assembled, respectively, in an aligned state, thereby forming a complete body as illustrated in FIG. 1 and FIG. 2. As illustrated in FIG. 3 for example, fixing of the lower case part 14 to the intermediate case part 12 is achieved by engaging locking projection pieces 14a provided along a peripheral edge of the upper opening of the lower case part 14 to recesses to be locked (not illustrated) provided on a lower opening side of the intermediate case. The fixing structure of the upper case to the intermediate case is of a similar structure.

In the casing 10, a driving mechanism D and the rotating holder 30 rotated and driven by the driving mechanism are housed.

The driving mechanism D includes elements such as a circuit board (a main circuit board 110 and a sub-circuit board 120) 100, the motor 50 connected to the main circuit board 110 with motor wires 52, the battery 70 connected to the sub-circuit board 120 with battery wires 72, and the angular speed sensor (gyro sensor) 61 mounted on the main circuit board 110. In this example, a rotation speed of the motor 50 is adjusted by PWM (pulse width modulation) control. The driving mechanism D is supported by an inner case 80 that is fixed in the casing 10 by screwing or the like.

The circuit board 100 includes the control unit (main control circuit) 60, the main circuit board 110 on which the angular speed sensor 61 and the like are mounted, and the sub-circuit board (USBPCB) 120 for charging.

The rotating holder 30 is a rotor having an inverted-bowl shape having a lower side being open, and includes a sampler holder 32 having a recessed lower face in which one end of the sperm sampler 200 is engaged to hold the sperm sampler, a bottom cylinder 34 fixed to a peripheral edge of a lower opening of the sampler holder, and a coupling 36 that is fixed onto an upper-face center part of the sampler holder by screwing and has a center hole into which an output shaft of the motor is inserted and fixed. By cooperation of the sampler holder 32 and the bottom cylinder 34, the bottom part of the sperm sampler is fitted and held in a stable state with the center axis CL of the driving device 1 and the center axis CL of the sperm sampler being coaxially aligned. Further, when the rotating holder 30 is rotated by receiving a driving force from the motor via the coupling 36, because the rotating holder 30 stably rotates while eccentric rotation is regulated by an inner face of the casing 10, even eccentric rotation of the sperm sampler being held is effectively prevented.

The inner case 80 is fixed in the intermediate case part 12 by screwing or the like, and includes a motor housing part 82, a battery housing part 84, and a circuit-board attaching part 86, and the like.

A round hole 12a is formed while penetrating an appropriate position of the intermediate case part 12, and the switch piece (switch) 20 is fitted in the hole. While the switch piece is in a state of projecting outward in the round hole at normal time, when the switch piece is pressed inward, a switch part (changeover switch, see FIG. 10) 67 on the main circuit board is turned ON. When pressing on the switch piece is released, the switch returns to the projecting position by a spring (not illustrated) to turn OFF the switch part 67. The main circuit board 110 is arranged at a position opposing the round hole 12a in the casing, and an LED lens 22 is arranged between the round hole 12a and the main circuit board 110 so as to diffuse emitted light from an LED on the main circuit board toward the switch piece side. The switch 20 is lighted up by light emission of the LED when the switch part is in an ON state, and an operator can be aware that operation of the driving device 1 is available.

Figure 10:
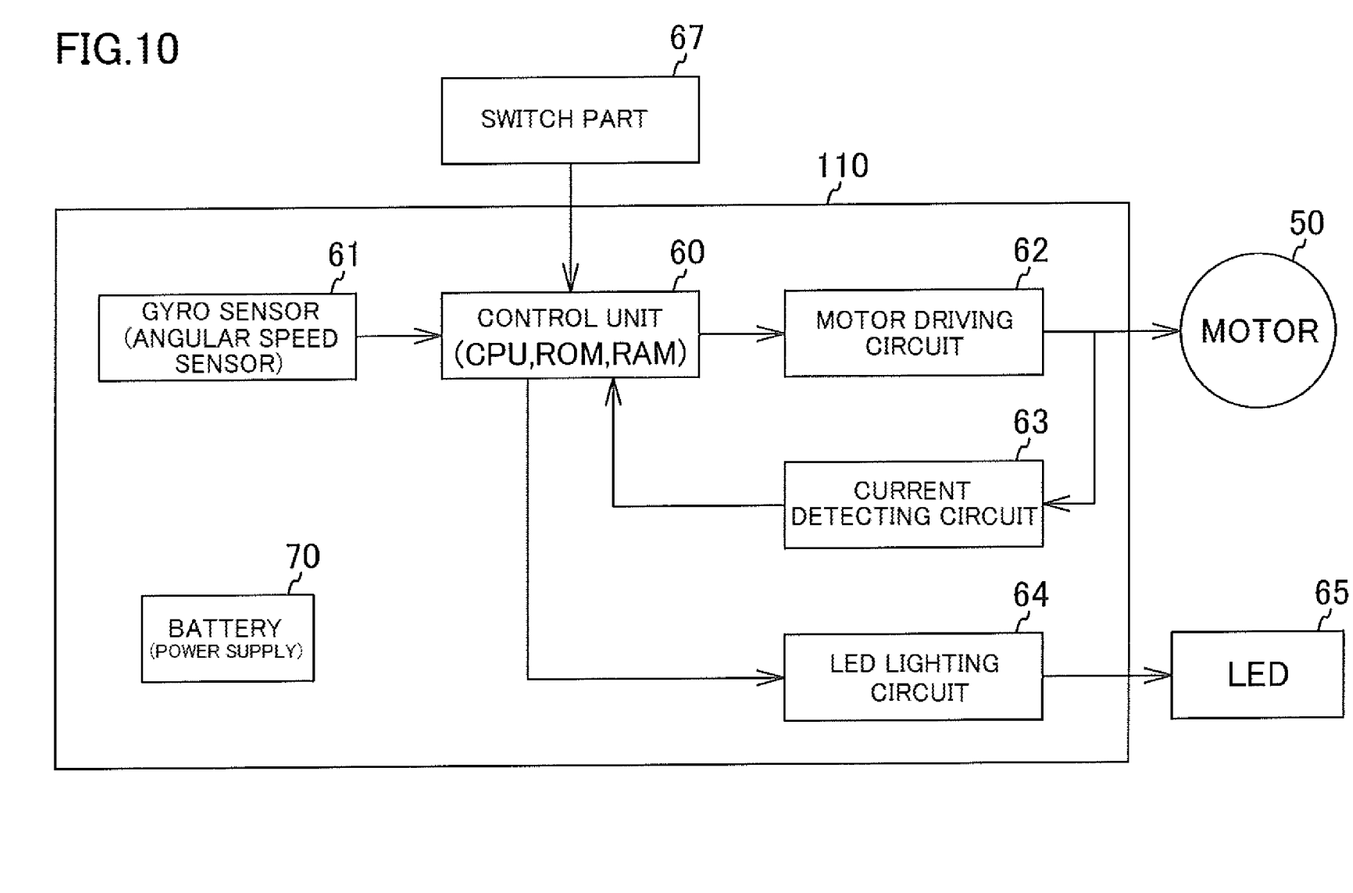
FIG. 10 is a block diagram illustrating a configuration of a control system of the sperm sampler driving device.

As illustrated in the block diagram of FIG. 10, the main circuit board 110 has incorporated therein elements such as the control unit (a CPU, a memory, and the like) 60 as a main control unit, the angular speed sensor 61, a motor driving circuit 62, a current detecting circuit 63, an LED lighting circuit 64, an LED 65, and the switch part (changeover switch) 67. The main circuit board 110 and the motor 50 are electrically connected to each other with the motor wires 52. The sub-circuit board 120 is a circuit board for charging that is connected electrically to the battery 70 via the battery wires 72. By connecting a lead terminal of a charger to a charging terminal 25 arranged in a small hole 24 provided in a rear face of the casing, the battery is charged through the sub-circuit board.

One characteristic of the sperm sampler driving device 1 having the configuration described above is that the sperm sampler driving device 1 is a unit that detachably holds the sperm sampler 200 and rotates the held sperm sampler, where the sperm sampler driving device 1 includes the casing 10 that has one end being open and is manually holdable, the rotating holder 30 that is rotatably arranged in the opening of the casing and detachably holds a part of the sperm sampler, the motor 50 that is arranged in the casing and rotates and drives the rotating holder, the control unit 60, the battery 70 as power supply for the motor and the control unit, the single switch 20, 67 that is arranged on an outer face of the casing and turns on and off power supply from the battery to the motor, and the angular speed sensor 61 that detects a turning angular speed of the casing, in which the control unit changes a rotation direction and a rotation speed of the motor according to a change in the turning angle of the casing.

Another characteristic of the present invention is that the control unit 60 obtains, as an initial original point, a turning angle of the casing 10 (the driving device 1) that is detected by the angular speed sensor 61 at a time point when the switch 20, 67 is turned ON, and when the casing is turned from the initial original point to one direction or another direction, the control unit controls the turning direction and rotation speed of the motor based on an angular difference from the initial original point after the turning, and when the turning angle of the casing exceeds a predetermined value (an initial maximum turning angle), the control unit moves the original point in the same direction from the initial original point by an angle exceeding the predetermined value.

<Configuration of Sperm Sampler>

FIG. 5A to FIG. 5E are respectively a front view, a top view, a bottom view, a perspective view, and a B-B cross sectional view illustrating a configuration of one example of a sperm sampler applicable to the driving device.

The sperm sampler 200 is substantially constituted of a case 202 made of relatively rigid plastic, a core member 210 housed in the plastic case, and a cushion member 220 arranged between the core member and the case.

The case 202 includes a case body 204 that has a long size and one end (upper end) being open, and a cap 206 that is attached to and detached from an opening of the case body. The other end (lower end) of the case body, that is, a bottom face 204a, has dimensions and shape that are set to be elastically attachable to and detachable from the inside of a recessed portion of the rotating holder 30 that is arranged in the lower opening of the driving device 1 in an exposed manner.

FIGS. 6A to 6D illustrate a state where the bottom face 204a of the sperm sampler is held by the rotating holder 30 of the driving device 1, and in this holding state, the driving device and the sperm sampler are configured so that the center axis CL of the driving device and the center axis CL of the sperm sampler 200 match each other and located on the same axis. With this configuration, eccentric rotation of the sperm sampler at the time of rotating and driving the rotating holder 30 can be prevented, and variations and deviations of sliding and rubbing between the core member 210 and a penis can be prevented, thereby improving the stability when the device is used.

The core member 210 is constituted of a gel-like resin such as elastomer, and includes a penis insertion hole 212 and an insertion cavity 214 connected to the inside of the penis insertion hole. The core member 210 is housed in the case body 204 so that the penis insertion hole 212 is directed toward the opening side of the case body. When in use, the cap 206 is removed to expose the penis insertion hole, and a penis is inserted therein. In this state, a container main body is held by a user and moved in an axial direction and rotated by using the driving device 1, so as to repeat a sliding and rubbing movement between an inside wall of the cavity and the penis to facilitate ejaculation.

<Operating Procedure for Rotation Speed Adjustment and Switching of Rotation Direction>

Figure 6A:
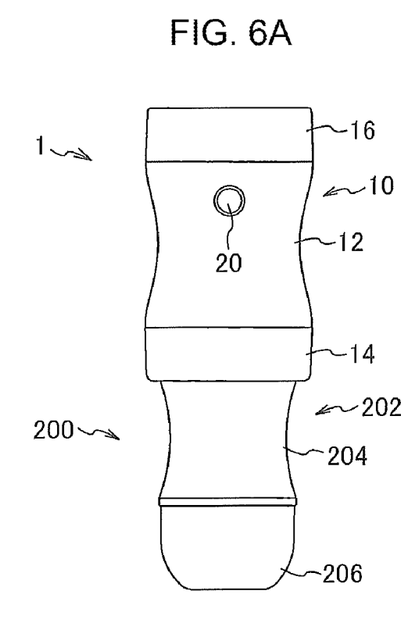
FIG. 6A and FIG. 6B are respectively a front view and a perspective view illustrating a state that the sperm sampler is attached to the sperm sampler driving device.
Figure 6B:
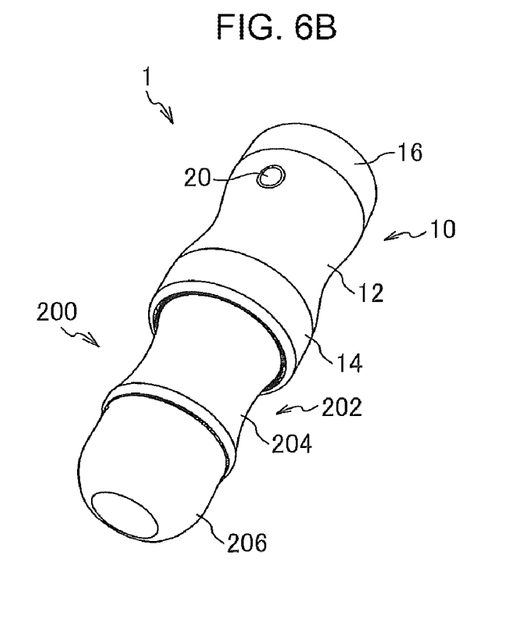
Figure 6C:
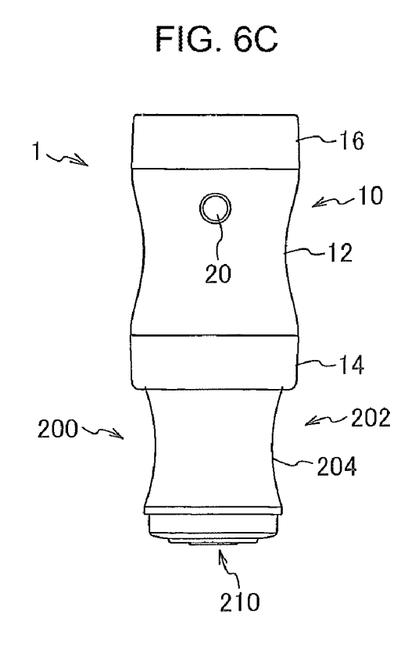
FIG. 6C and FIG. 6D are respectively a front view and a perspective view illustrating a state where a cap of the sperm sampler is removed.
Figure 6D:
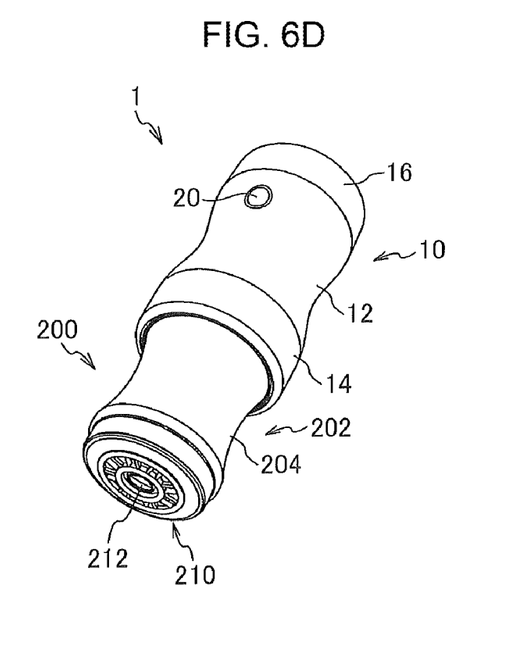
Figure 7:
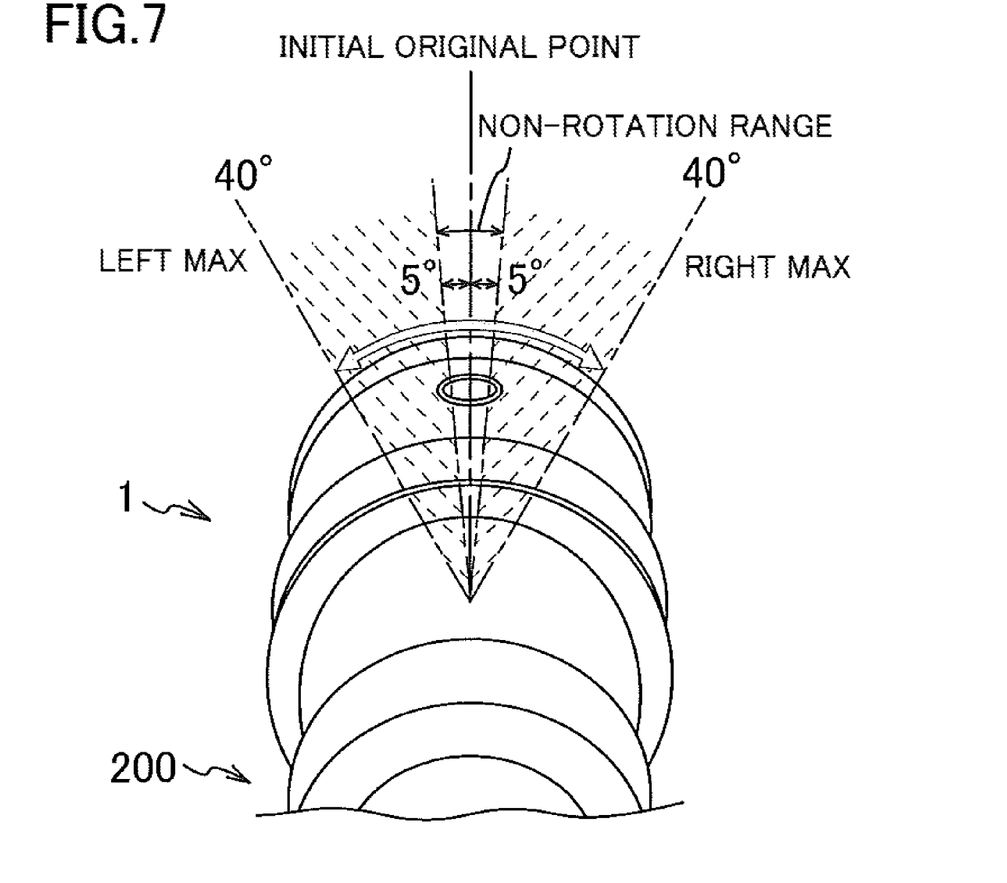
FIG. 7 is an explanatory diagram of an operating angle range of the sperm sampler driving device.
Figures 8A, 8B:
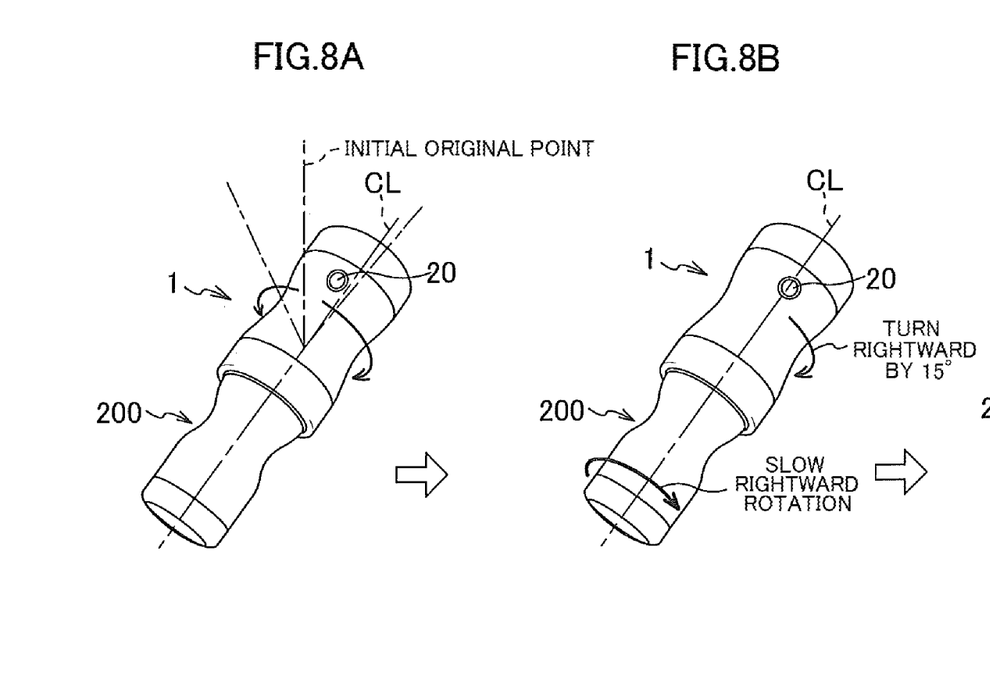
FIG. 8A, FIG. 8B, and FIG. 8C are explanatory diagrams illustrating an operating procedure and a rotating movement for rotating the sperm sampler in one direction.
Figure 8C:
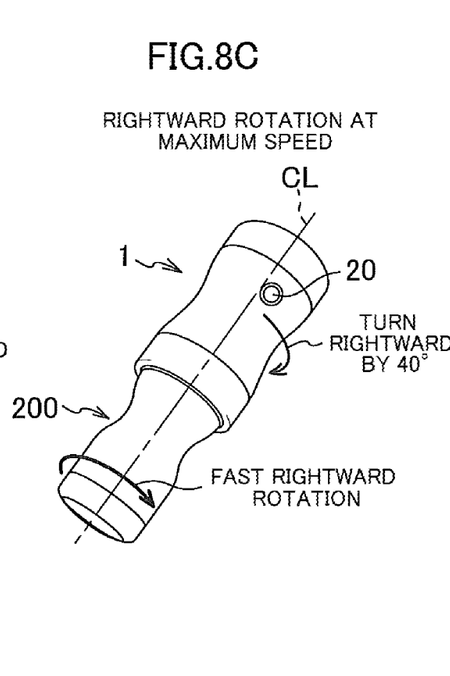
Figures 9A, 9B, 9C:
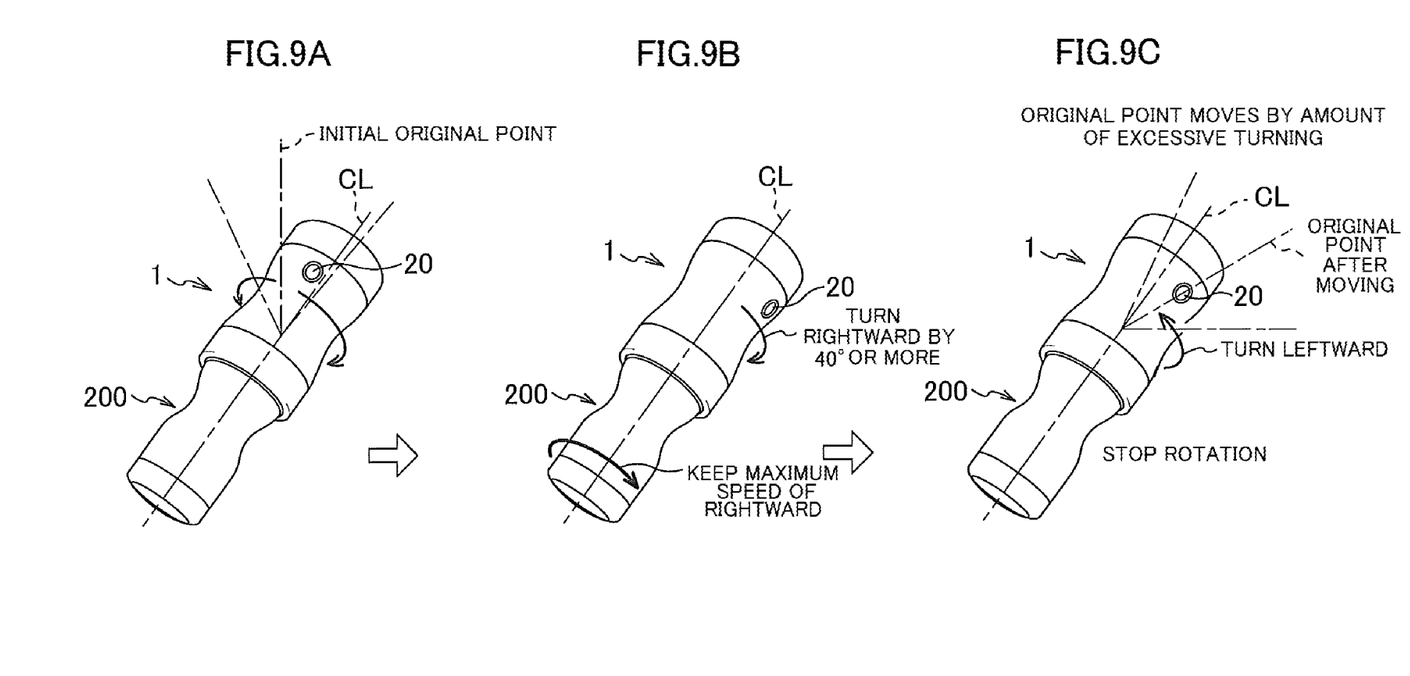
FIG. 9A, FIG. 9B, and FIG. 9C are explanatory diagrams illustrating an operating procedure and a movement when an initial maximum rotating movement angle is exceeded.
Figure 11:
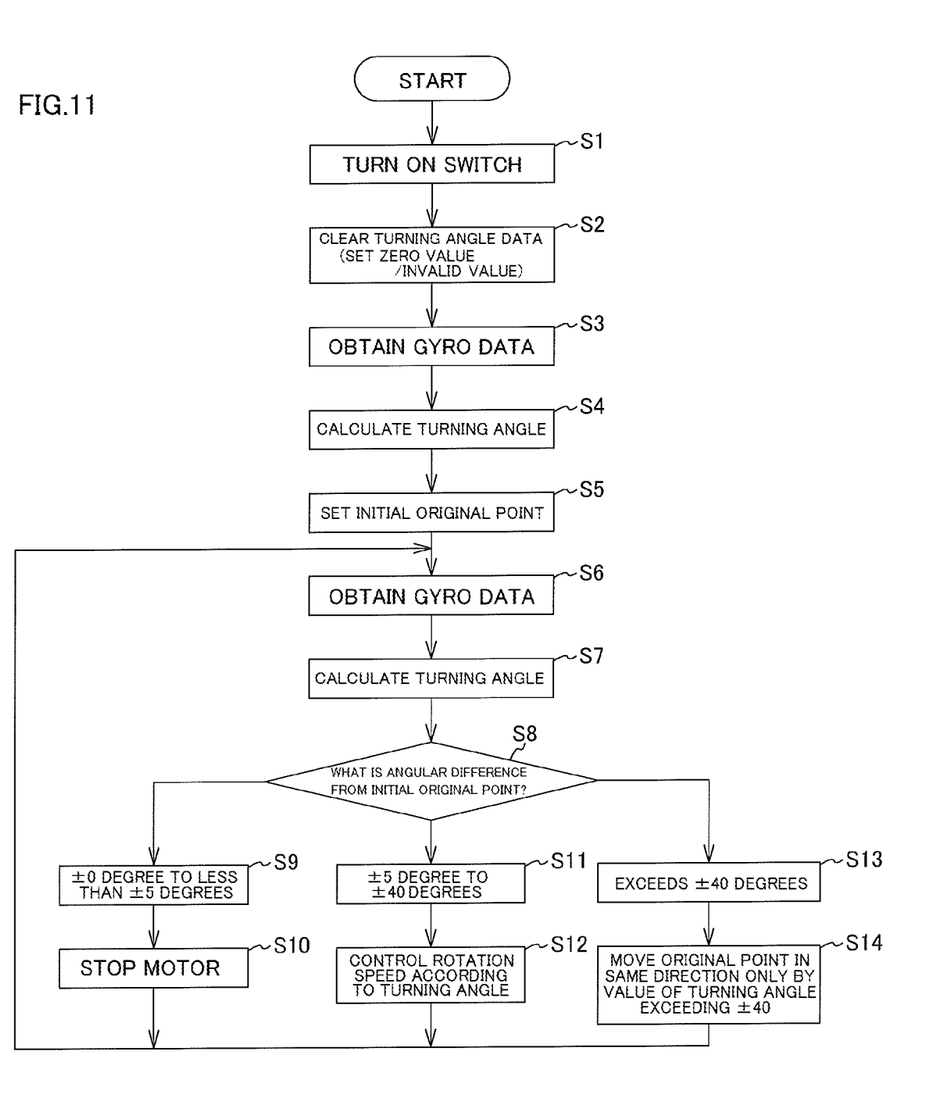
FIG. 11 is a flowchart illustrating an operating procedure of the sperm sampler driving device.

FIG. 6A and FIG. 6B are respectively a front view and a perspective view illustrating a state where the sperm sampler is attached to the sperm sampler driving device, and FIG. 6C and FIG. 6D are respectively a front view and a perspective view illustrating a state where a cap of the sperm sampler is removed. FIG. 7 is an explanatory diagram of an operating angle range of the sperm sampler driving device, FIG. 8A, FIG. 8B, and FIG. 8C are explanatory diagrams illustrating an operating procedure and a rotating movement for rotating the sperm sampler in one direction, and FIG. 9A, FIG. 9B, and FIG. 9C are explanatory diagrams illustrating an operating procedure and a movement when an initial maximum rotating movement angle is exceeded. FIG. 10 is a block diagram illustrating a configuration of a control system of the sperm sampler driving device, and FIG. 11 is a flowchart illustrating an operating procedure of the sperm sampler driving device.

As illustrated in FIG. 6, the bottom part 204a of the sperm sampler 200 is fitted in the recessed portion of the rotating holder 30 of the driving device 1, so that the sperm sampler 200 can be held without falling off in a state where respective center axes CL of the driving device 1 and the sperm sampler match each other. By holding down the switch 20 to turn on the power to drive the motor 50, the rotating holder 30 can be rotated in one direction (clockwise) or in another direction (counterclockwise). To turn OFF the power, the switch 20 is held down.

In this example, the motor 50 does not start its rotation by only turning on the power, and by performing an operation to rotate the driving device 1 about the center axis CL by a predetermined angle (5 degrees in this example) or more in a clockwise direction or a counterclockwise direction from the initial original point (FIG. 7), the rotating holder starts to rotate in the clockwise or counterclockwise direction. Even when the driving device 1 is turned by less than a range (a non-rotation range) of the predetermined angle rightward or leftward, 5 degrees in this example, from the initial original point, the motor does not drive. The motor 50 starts to rotate when the driving device 1 is turned while exceeding the non-rotation range of 5 degrees rightward or leftward. The rotation speed of the rotating holder 30 can be sequentially increased by turning the driving device 1 in a rightward direction or a leftward direction from the original point within a range of 35 degrees up to a maximum of 40 degrees (an initial maximum turning angle) from the original point, and when the turning angle exceeds 40 degrees from the initial original point, the speed is not increased any further and a maximum speed (for example, 200 rpm) is maintained. In order to decelerate or stop the rotating holder that is rotating, it is only necessary to turn the driving device 1 in reverse toward the initial original point to reset the turning angle.

In order to switch the rotation direction of the rotating holder 30 rotating in one direction to a reverse direction, the switching can be achieved by turning the driving device 1 in the reverse direction of the hitherto turning direction about the center axis CL by exceeding 5 degrees from the initial original point.

A change in the turning angle of the driving device 1 is detected by the angular speed sensor 61, and based on this detection signal, the control unit can control the motor driving circuit 62 to achieve the switching. In this example, immediately after the turning angle exceeding the non-rotation range, the pulse width of a motor control signal supplied from the motor driving circuit 62 to the motor 50 is 20%, and the pulse width of the motor control signal when the turning angle becomes more than 40 degrees from the initial original point is 100%.

An operating procedure of the driving device 1 is described with reference to FIG. 9 and FIG. 10.

First, a user manually holds the driving device 1 with the sperm sampler 200 being set in the recessed portion of the rotating holder 30 in a state where the power is not turned ON, and inserts his penis in the penis insertion hole 212 of the core member 210. In this setting completed state, by holding down the switch 20 (for 0.8 second, for example) to turn ON the power, it becomes possible to start operation of the driving device 1.

First, at Step S1, by holding down the switch 20, a current is supplied from the battery 70 to the motor 50 and the circuit board 100, thereby making a state where the main circuit board 110 on which the control unit 60, the angular speed sensor 61, and the like are mounted becomes operable.

At this stage, the control unit 60 clears turning angle data stored in the memory thereof (Step S2).

At Step S3, the angular speed sensor 61 obtains data (gyro data) related to a current turning angle of the driving device 1 (the casing 10 and the rotating holder 30), and the control unit calculates the current turning angle based on the gyro data, thereby setting the current turning angle as an initial original point (Steps S4, S5).

Thereafter, when the user turns the driving device 1 by a predetermined angle in any of rightward and leftward directions beyond the initial original point, the control unit 60 obtains, from the angular speed sensor 61, gyro data related to the angle after the turning is performed, calculates the turning angle (Steps S6, S7), and checks an angular difference between the initial original point and the current turning angle at Step S8.

Based on the result of checking the angular difference at Step S8, the control unit controls the motor as follows. In this example, the rotating holder rotates clockwise by turning in a positive direction of the driving device 1 and rotates counterclockwise by turning in a negative direction of the driving device 1.

First, when the angular difference between the initial original point and the current turning angle is within a range of ±0 to ±5, a state where the motor is stopped is maintained (Steps S9, S10).

As described above, the rotation speed (rpm) is adjusted in a range of 0 rpm to 200 rpm by the PWM control according to a change in the turning angle.

While the motor is stopped when the turning angle is within the range of ±5 degrees, immediately after the turning angle exceeds ±5 degrees, the pulse width of the motor control signal is set to 20%.

When the angular difference between the initial original point and the current turning angle is within a range of ±5 to ±40 degrees, the motor is controlled at a rotation speed according to the turning angle (Steps S11, S12). For example, the rotation speed is controlled by sequentially increasing and decreasing the pulse width of the motor control signal from 20% to 100%, with the angular difference being in the range of ±5 to ±40 degrees with reference to the initial original point (see FIGS. 8B and 8C)).

When the angular difference between the initial original point and the current turning angle exceeds ±40 degrees with reference to the initial original point, the rotation speed of the rotating holder is maintained at 200 rpm that is the maximum speed (Step S13, FIG. 9A and FIG. 9B). However, the initial original point is controlled to move in the same direction by an amount of the turning angle of the driving device 1 exceeding ±40 degrees, for example, by 10 degrees when the turning angle exceeds ±40 degrees by 10 degrees (Step S14).

For example, when the driving device 1 is turned in the rightward direction from a first initial original point to positive 50 degrees, the original point moves by 10 degrees in the positive direction from a first angular position, and thus the new original point becomes the reference when there is an operation to return to the negative direction to decelerate the rotating holder. In this case, the non-rotation range is displaced by 10 degrees in the positive direction from a first non-rotation range, and thus the motor can be stopped by returning in the negative direction by 35 degrees from the rotation angle of positive 50 degrees. Therefore, the motor can be stopped without returning to the first original point in the negative direction by 45 degrees from the rotation angle of positive 50 degrees, thereby improving operability (FIG. 8C). When the angle range of manually holding and turning the casing exceeds 40 degrees rightward or leftward, the wrist becomes tired, and moving the original point enables easy operation within a reasonable angle range by turning in the range of 40 degrees rightward or leftward from a position and the posture of the wrist from which the operator can easily operate the casing.

The current detecting circuit 63 is configured to immediately stop the motor at any stage when the current detecting circuit 63 detects an abnormal current.

When it is desired to keep the rotation speed of the rotating holder when the rotation speed reaches a predetermined value, the rotation speed can be kept at a constant speed with a quick press of the switch 20. On the other hand, when it is desired to release the kept rotation speed, the keeping state can be released with another quick press of the switch 20.

Further, it is also possible to perform an operation of inverting the rotation direction in a state where the rotation speed is kept with a quick press of the switch 20. That is, in a state where the rotation speed is kept at a predetermined value in the rightward direction, by performing inversion-turning of the casing in the reverse direction by 40 degrees or more, the rotation direction of the rotating holder is inverted while the rotation speed is kept as it is.

<Summary of Configuration, Operation, and Effect of the Present Invention>

The sperm sampler driving device 1 according to a first aspect of the present invention is a unit that rotates a held sperm sampler, where the sperm sampler driving device 1 includes the casing 10, the rotating holder 30 that is rotatably arranged in an opening of the casing and detachably holds a part of the sperm sampler, the motor 50 that rotates and drives the rotating holder, the control unit 60, the battery 70, the single switch 20, 67, and the angular speed sensor 61 that detects a turning angular speed of the casing, in which the control unit changes a rotation direction and a rotation speed of the motor according to a change in a turning angle of the casing.

After the switch is turned on to turn on the power of the sperm sampler driving device, the rotating speed and the rotation direction can be changed with a simple operation of changing the turning angle of the driving device itself without performing any complicated switch operations, thereby improving the massaging effect for a penis. Particularly, because it is a configuration to rotate the rotating holder based on information related to the turning angle and the turning direction obtained by the angular speed sensor, the device can be reduced in size and its configuration can be simplified. Because the number of switches is one and this switch is mainly used for turning on and off the power, complicated operations due to operating a plurality of switches as in conventional products are not required.

In the sperm sampler driving device 1 according to a second aspect of the present invention, the control unit obtains, as an initial original point, a turning angle of a casing that is detected by an angular speed sensor at a time point when a switch is turned ON, and when the casing is turned from the initial original point to one direction or another direction, the control unit controls switching of the turning direction and rotation speed of a motor based on an angular difference from the initial original point after the turning, and when the turning angle of the casing exceeds a predetermined value (an initial maximum turning angle), the control unit moves the original point in a same direction from the initial original point by an angle exceeding the predetermined value.

For example, in a turning range from 5 degrees to 40 degrees with reference to the initial original point, the rotation speed of the rotating holder is sequentially increased according to the turning angle, for example, and at a time point when reaching 40 degrees (the predetermined value), the rotation speed is set to a maximum rotation speed. When the driving device is turned in the same direction exceeding 40 degrees, the maximum speed does not change. On the other hand, when the device is turned in a returning direction from 40 degrees, the speed is decreased to a rotation speed according to the turning angle, and at a time point when the device is returned by an angle of 35 degrees, rotation of the rotating holder can be stopped. A range of ±5 degrees from the initial original point is defined as a non-rotation range, and the rotating holder does not rotate in this range.

Further, when the driving device is turned while exceeding 40 degrees from the initial original point, the original point is moved by an angle exceeding 40 degrees, and thus the motor can be stopped by turning the device by 35 degrees in a returning direction. When the original point is fixed, it becomes difficult to operate the device and the hand of an operator becomes tired; however, according to the present invention, such problems can be eliminated.

What is claimed is:

1. A sperm sampler driving device that detachably holds a sperm sampler and rotates a held sperm sampler, the sperm sampler driving device comprising:
   a casing that has one end being open and is manually holdable;
   a rotating holder that is rotatably arranged in an opening of the casing and detachably holds a part of the sperm sampler;
   a motor that is arranged in the casing and rotates and drives the rotating holder;
   a control unit;
   a battery as power supply for the motor and the control unit;
   a single switch that is arranged on an outer face of the casing and turns on and off power supply from the battery to the motor; and
   an angular speed sensor that detects a turning angular speed of the casing, wherein
   the control unit changes a rotation direction and a rotation speed of the motor according to a change in a turning angle of the casing.

2. The sperm sampler driving device according to claim 1, wherein
   the control unit obtains, as an initial original point, a turning angle of the casing that is detected by the angular speed sensor at a time point when the switch is turned ON,
   when the casing is turned from the initial original point to one direction or another direction, the control unit controls switching of a turning direction and a rotation speed of the motor based on an angular difference from the initial original point after turning, and
   when the turning angle of the casing exceeds a predetermined value, the control unit moves the original point in a same direction from the initial original point by an angle exceeding the predetermined value.

* * * * *